(12) United States Patent
West et al.

(10) Patent No.: US 6,273,877 B1
(45) Date of Patent: Aug. 14, 2001

(54) EPIDURAL NEEDLE WITH SECONDARY BEVEL

(75) Inventors: David Allen West, Columbus, NE (US); Michael Joseph Honey, Berkeley Heights, NJ (US); Daniel Lee Redowl, Columbus, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/620,511

(22) Filed: Jul. 20, 2000

(51) Int. Cl.$^7$ .................................................. A61M 25/00
(52) U.S. Cl. ............................................................. 604/264
(58) Field of Search ............................ 604/264, 51, 158, 604/164, 165, 170, 272, 273, 274, 44, 49, 169

(56) References Cited

U.S. PATENT DOCUMENTS 4,721,506 * 1/1988 Teves ...................................... 604/51
5,843,048 12/1998 Gross .................................... 604/264

* cited by examiner

*Primary Examiner*—Manuel Mendez
(74) *Attorney, Agent, or Firm*—Eric M. Lee

(57) ABSTRACT

An epidural needle is provided with a curved distal end to facilitate placement of a catheter into the epidural space of a spine. The distal end is further characterized by a primary bevel aligned to the longitudinal axis of the epidural needle at an angle of approximately 10°. A secondary bevel also is provided at the extreme distal end of the needle. The secondary bevel is aligned to the longitudinal axis of the needle at an angle of between 60°–80°. The curve, the primary bevel and the secondary bevel all are symmetrical about common plane passing through the longitudinal axis of the needle. The secondary bevel aligned at an angle of 60°–80° to the longitudinal axis provides a sufficiently sharp point to penetrate easily into the epidural space, but provides sufficient blunting to avoid inadvertent damage to the dura matter.

11 Claims, 2 Drawing Sheets

EPIDURAL NEEDLE WITH SECONDARY BEVEL

BACKGROUND OF THE INVENTION

1. Field of the Invention

The invention relates to an epidural needle for administering a liquid anesthesia into the epidural space of a spine.

2. Description of the Related Art

There are two optional procedures for administering a liquid anesthesia into the epidural space of a spine. In the first procedure, an epidural needle is inserted into the epidural space, and the anesthesia is administered directly through the epidural needle. The second procedure employs an epidural needle to introduce a catheter into the epidural space. The epidural needle then is withdrawn, and the catheter is left in place. The catheter then may be used to administer anesthesia over a longer period of time.

Care must be taken with both optional approaches to avoid penetrating the dura matter, which is a delicate membrane over the arachnoid. A puncture of the dura matter can cause a leakage of spinal fluid and various post-operative problems, such as severe headaches.

U.S. Pat. No. 4,721,506 shows an epidural needle for the direct administration of a liquid anesthesia into the epidural space. This prior art needle cannula is symmetrically generated about a linear longitudinal axis, and includes a generally planar bevel at the distal end. The bevel intersects the longitudinal axis of the needle at an angle of approximately 45°. The extreme tip defined by the bevel then is blunted at an angle of 80°–100° to the longitudinal axis and is rounded slightly from side-to-side. The blunting and rounding of the distal tip is intended to reduce the risk of inadvertent damage to the dura mater.

The prior art epidural needle for introducing a catheter into the epidural space differs from the configuration shown in U.S. Pat. No. 4,721,506 in several respects. First, a needle for introducing a catheter typically must be cross-sectionally larger than the epidural needle for the direct administration of a liquid anesthesia. For example, an epidural needle for introducing a catheter typically will have a gauge size of about 17–18 gauge (iso-9626). Additionally, a catheter that is urged axially beyond the end of a linear needle conceivably could damage the dura matter. Consequently, the prior art epidural needle for introducing a catheter typically will be configured to direct the catheter at an angle to the axis of the needle. The requirement for directing the catheter at an angle further complicates the various design requirements of the needle. First, the distal tip of the needle must be sufficiently sharp to penetrate of outer layers of the skin and then to enable penetration of the ligamentum flavum without significant trauma to the tissue. Second, the distal end must be curved to direct the catheter into an off-axis alignment. Third, the distal tip must be sufficiently blunted to minimize the potential for inadvertent contact-related damage to the dura mater.

A prior art attempt for accommodating these different competing objectives is shown in U.S. Pat. No. 5,843,048 which is directed to a needle for introducing a catheter into the epidural space. A side wall of the epidural needle shown in U.S. Pat. No. 5,843,048 is curved near the distal tip of the needle. A bevel then is formed to intersect the curved side wall at the distal tip. Finally, the extreme distal end where the beveled surface and the curved side wall intersect is blunted to define a secondary bevel surface. The secondary bevel shown in U.S. Pat. No. 5,843,048 defines a substantially planar surface that is aligned to the longitudinal axis of the needle at an angle of approximately 80°–100°. Thus, the plane defined by the secondary bevel lies within a 10° variation from a plane passing perpendicularly through the longitudinal axis. This is substantially the same angular alignment of blunting employed on the straight epidural needle disclosed in U.S. Pat. No. 4,721,506.

The blunting or secondary bevel on the prior art epidural needles both are intended to minimize the risk of damage caused by inadvertent contact with the dura matter. However, the prior art blunt tip also necessitates a substantially higher force for the initial penetration of the skin and for puncturing the ligamentum flavum. The requirement for higher forces with the prior art blunted epidural needle necessarily implies greater trauma to the patient. Furthermore, the greater forces that must be exerted on the prior art epidural needle creates the potential that the prior art epidural needle will accelerate after penetrating the ligamentum flavum, and hence will be propelled into the dura matter. Thus, the blunted tip can actually lead to the dural puncture that the prior art blunted tip is intended to avoid.

In view of the above, it is an object of the subject invention to provide an epidural needle with a distal end configured to both facilitate entry into the epidural space and reduce risk of damage to the dura mater.

SUMMARY OF THE INVENTION

The subject invention relates to an epidural needle for inserting a catheter into the epidural space. The epidural needle has opposed proximal and distal ends and a lumen extending therebetween. The proximal end of the needle is mounted to a hub with a through passage that aligns axially with the lumen through the needle. The hub is dimensioned and configured to facilitate secure gripping and maneuvering of the epidural needle.

The epidural needle may be used with a solid semi-rigid stylet that can be telescoped into the lumen of the epidural needle. The stylet substantially fills the lumen and is intended to prevent coring that might otherwise occur as the epidural needle enters tissue of the patient. The stylet may have a proximal end with a sytlet hub mounted thereto. The stylet hub may be configured for releasable mating with the hub of the epidural needle.

The epidural needle of the subject invention is substantially cylindrical along a major portion of its length from the proximal end toward the distal end. Hence, the needle is concentric about a substantially linear longitudinal axis for a major portion of the length of the needle.

The subject invention relates primarily to the configuration of the distal end of the epidural needle. In particular, the distal end of the subject epidural needle is curved about an axis that is offset from and orthogonal to the longitudinal axis. The distal end of the epidural needle also is characterized by a substantially planar primary bevel. The primary bevel and the curved distal wall preferable are substantially symmetrical about a common plane extending through an axis of the epidural needle. The plane defining the primary bevel preferably intersects the longitudinal axis of the needle at an angle in the range of 8°–12°, and preferably about 10°. Additionally, the primary bevel may be disposed such that the distal opening to the lumen defined by the primary bevel is offset from the longitudinal axis of the needle. As a result, the distal opening to the subject epidural needle is aligned at an acute angle to the longitudinal axis of the needle. Consequently, a catheter directed through the lumen of the epidural needle will be curved or diverted transversely from the axis of the needle and will be guided into a desired position within the epidural space.

The distal end of the epidural needle further includes a secondary bevel at the extreme distal end of the needle. The secondary bevel also is substantially symmetrical about the plane of symmetry of both the primary bevel and the curve at the distal end. The secondary bevel is aligned to the longitudinal axis of the needle at an angle of greater than 60°, but less than 80°. The secondary bevel formed at a 60°–80° angle to the longitudinal axis of the needle provides sufficient blunting to avoid damage to the dura matter. However, unlike the prior art, a 60°–80° angle of the secondary bevel provides a sufficiently sharp distal end to facilitate initial penetration into the skin and through the ligamentum flavum without difficulty for the anesthesiologist and with little risk of excessive force urging the epidural needle through the ligamentum flavum, through the epidural space and into damaging contact with the dura matter.

DETAILED DESCRIPTION

Figure 1:
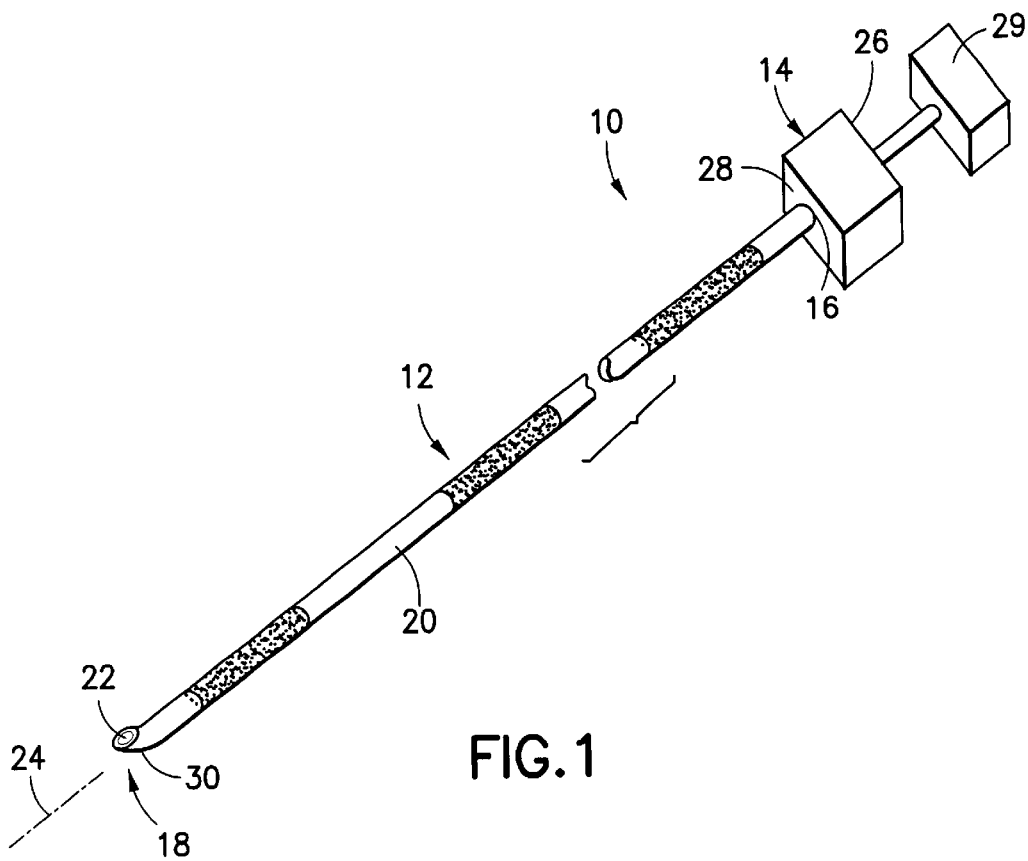
FIG. 1 is a perspective view of an epidural needle in accordance with the subject invention.
Figure 5:
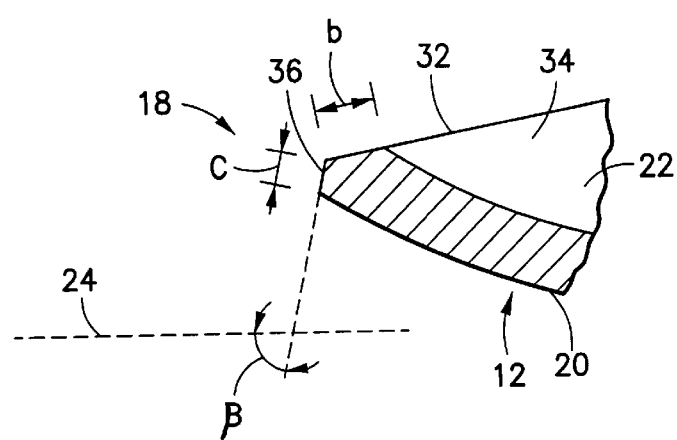
FIG. 5 is a cross-sectional view similar to FIG. 4, but showing only the extreme distal end of the epidural needle.

An epidural needle assembly in accordance with the subject invention is identified generally by the numeral 10 in FIG. 1. Epidural needle assembly 10 includes an elongate epidural needle 12 and a needle hub 14. Epidural needle 12 preferably is a 17 or 18 gauge needle with an overall length of about 3.5 inches. Needle 12 includes a proximal end 16, a distal end 18 and a side wall 20 extending between ends 16 and 18. Side wall 20 defines a lumen 22 extending from proximal end 16 to distal end 18 of epidural needle 12. Portions of side wall 20 from proximal end 16 to a location near distal end 18 are cylindrical. Hence lumen 22 and cylindrical portions of tubular side wall 20 are concentric with a linear longitudinal axis 24, as shown most clearly in FIGS. 1, 2, 4 and 5.

Proximal end 16 of epidural needle 12 is securely mounted to hub 14. More particularly, hub 14 includes a proximal end 26 that faces away from epidural needle 12, a distal end 28 that faces generally toward epidural needle 12 and a through passage (not shown). The through passage extends between proximal and distal ends 26 and 28 and communicates with lumen 22 of epidural needle 12. Proximal end 28 of hub 14 is configured to releasably engage the hub of a stylet 29 that can be urged axially into lumen 22 of epidural needle 12 to prevent coring during penetration of epidural needle 12 into tissue of a patient.

Figure 2:
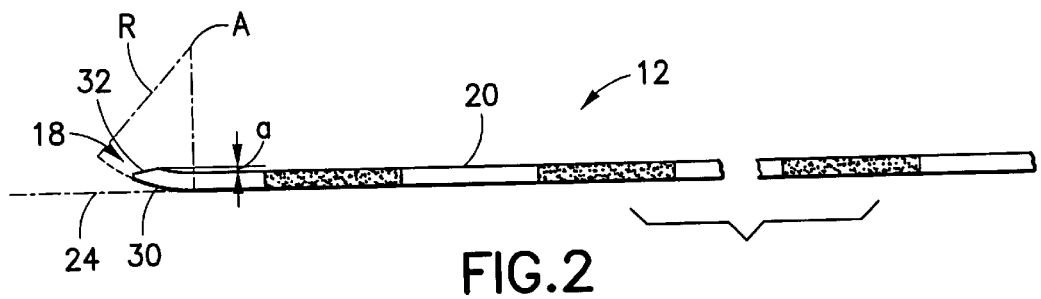
FIG. 2 is a side elevational view of the epidural needle.

Portions of side wall 20 of epidural needle 12 adjacent distal end 18 define a curve 30 that extends about an axis A that is orthogonal to and offset from longitudinal axis 24. More particularly, curve 30 defines a radius R of about 0.4 inch, and extends through an arc sufficient for the distal opening to lumen 22 to lie entirely on a side of longitudinal axis 24 closest to the axis A about which curve 30 is formed. Additionally, curve 30 produces an offset "a" on a side of epidural needle 12 of approximately 0.01 inch, as shown in FIG. 2. Furthermore, curve 30 is symmetrical about the plane identified by line 4—4 in FIG. 3.

Figure 3:
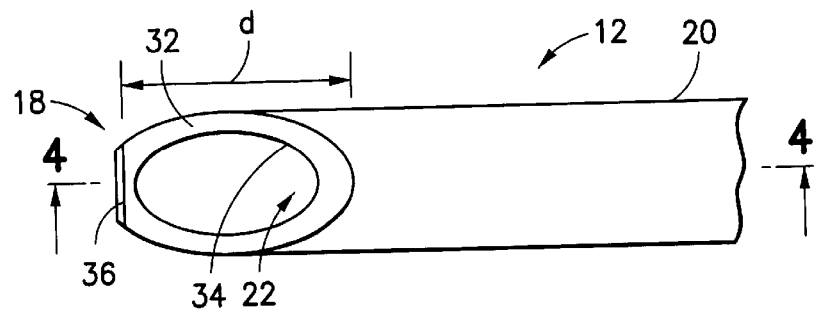
FIG. 3 is a top plan view of the distal end of the epidural needle.
Figure 4:
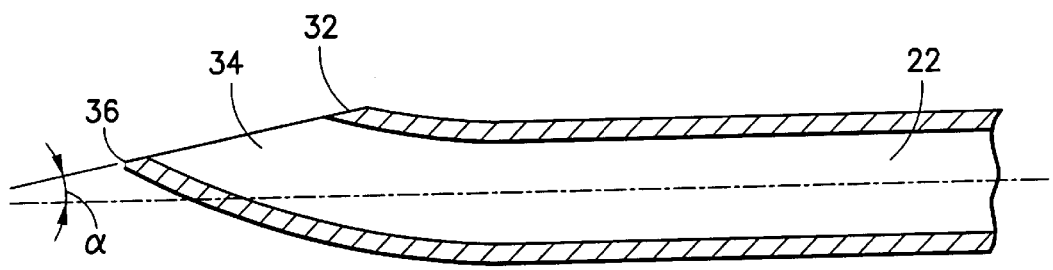
FIG. 4 is a cross-sectional view taken along line 4—4 in FIG. 3.

Distal end 18 of epidural needle 12 is further characterized by a planar primary bevel 32 that is symmetrical about the plane defined by line 4—4 in FIG. 3. Primary bevel 32 is aligned to longitudinal axis 24 and an angle "α" of 10°, as shown in FIG. 4. Additionally, primary bevel 32 is disposed to intersect side wall 20 at locations on one longitudinal side of longitudinal axis 24, and namely on the side of longitudinal axis 24 closer to the axis A about which curve 30 is formed. As a result, and as shown most clearly in FIGS. 3 and 4, epidural needle 12 defines a distal opening 34 that faces in an oblique direction. The existence of curve 30 and obliquely aligned distal opening 34 will cause a catheter urged through lumen 22 to deflect into an off-axis alignment as the catheter exits from distal opening 34.

Distal end 18 of epidural needle 12 is further characterized by a planar secondary bevel 36 at a location on primary bevel 32 diametrically opposite the axis A of curvature for curve 30 and substantially symmetrical with the plane defined by line 4—4 in FIG. 3. Secondary bevel 36 defines a plane aligned at an angle β of between 60°–80°, and preferably 70°–75° with respect to longitudinal axis 24 of epidural needle 12. Secondary bevel 36 must be positioned not to break into lumen 22, and preferably, in view of the above-described angles of bend and the angles of primary bevel 32, secondary bevel 36 is spaced distally from lumen 22 by a distance "b" of approximately 0.005 inch as measured along primary bevel 32. Therefore, secondary bevel 36 defines a thickness dimension "c", as measured along the plane of symmetry of approximately 0.003 inch. More particularly, secondary bevel 36 is aligned such that the most distal position on epidural needle 12 occurs where secondary bevel 36 intersects the outer surface of epidural needle 12. The blunting achieved by secondary bevel 36 results in a major dimension "d" on primary bevel 32 of about 0.091 inch for a 17 gauge needle and about 0.114 inch for an 18 gauge needle, as shown in FIG. 4.

The existence of secondary bevel 36 and the angular alignment of 60°–80° achieves several significant advantages. First, secondary bevel 36 provides an adequate degree of blunting to prevent inadvertent damage to the dura matter. Second, the alignment of 60°–80° achieves substantially greater sharpness than the 80°–100° secondary bevel specified by the prior art. The greater sharpness facilitates the initial penetration of the skin and the penetration of the ligamentum flavum without the local trauma that would otherwise be caused by penetration with a blunt instrument and without the significant force that could propel an epidural needle into the dura matter after the ligamentum flavum has been penetrated.

While the invention has been described with respect to a preferred embodiment, it is apparent that various changes can be made without departing from the scope of the invention as defined by the appended claims.

What is claimed is:

1. An epidural needle having a proximal end, a distal end and a tubular side wall extending therebetween, said side wall defining a lumen extending from said proximal end to said distal end, portions of said side wall extending from said proximal end substantially to said distal end being cylindrical and defining a substantially linear longitudinal axis, portions of said side wall at said distal end being curved, a primary bevel defined in said curve at said distal end and defining a distal opening to said lumen extending obliquely from said epidural needle, a secondary bevel at said distal end and extending from said primary bevel to outer surface portions of said epidural needle, said secondary bevel being aligned to said longitudinal axis at an angle between 60°–80°.

2. The epidural needle of claim 1, wherein said primary and secondary bevels each are substantially planar.

3. The epidural needle of claim 1, wherein said primary bevel defines a plane aligned to said longitudinal axis at an angle of 10°–12°.

4. The epidural needle of claim 3, wherein said plane defined by the primary bevel is aligned to said longitudinal axis at an angle of substantially 10°.

5. The epidural needle of claim 1, wherein said secondary bevel defines a plane aligned to said longitudinal axis at an angle of 70°–75°.

6. The epidural needle of claim 1, wherein said curve, said primary bevel and said secondary bevel all are substantially symmetrical about a common plane passing through said longitudinal axis.

7. An epidural needle having a proximal end, a distal end and a tubular side wall extending therebetween, said side wall defining a lumen extending from said proximal end to said distal end, portions of said side wall extending from said proximal end substantially to said distal end being cylindrical and defining a substantially linear longitudinal axis, portions of said side wall at said distal end defining a curve formed about an axis of curvature offset from and substantially orthogonal to said longitudinal axis, a primary bevel defined on said curve at said distal end and, said primary bevel being offset from said longitudinal axis and defining a plane aligned to said longitudinal axis at an angle of approximately 10°, said epidural needle further comprising a substantially planar secondary bevel at said distal end of said epidural needle, said secondary bevel intersecting said primary bevel and defining a plane aligned to said longitudinal axis at an angle of between 60°–80°, said primary bevel, said secondary bevel and said curve being symmetrical about a plane passing through said longitudinal axis of said needle.

8. The epidural needle of claim 7, wherein said axis of curvature is spaced from said longitudinal axis of said needle sufficiently for defining a radius of curvature of approximately 0.4 inch.

9. The epidural needle of claim 7, wherein the epidural needle is a 17 gauge needle.

10. The epidural needle of claim 7, wherein the epidural needle is a 18 gauge needle.

11. The epidural needle of claim 7, wherein said epidural needle has an outer surface, said secondary bevel intersecting said outer surface at a location defining the distal end of the epidural needle.

\* \* \* \* \*